(12) United States Patent
Abulhaj

(10) Patent No.: US 7,232,420 B1
(45) Date of Patent: Jun. 19, 2007

(54) MULTIPLE FLOW RATE SELECTION VALVE

(76) Inventor: Ramzi Abulhaj, 8935 NW. 27th St., Miami, FL (US) 33172

( * ) Notice: Subject to any disclaimer, the term of this patent is extended or adjusted under 35 U.S.C. 154(b) by 0 days.

(21) Appl. No.: 11/026,199

(22) Filed: Dec. 30, 2004

(51) Int. Cl.
*A61M 39/00* (2006.01)
*A61M 39/22* (2006.01)

(52) U.S. Cl. ............... 604/32; 604/246; 604/247; 604/248

(58) Field of Classification Search ............ 604/32–33, 604/246, 247, 248–256, 257, 892.1, 892.16
See application file for complete search history.

(56) References Cited

U.S. PATENT DOCUMENTS

| | | | | |
|---|---|---|---|---|
| 5,098,407 A | * | 3/1992 | Okamura | 604/248 |
| 5,478,318 A | * | 12/1995 | Yoon | 604/167.05 |
| 6,142,980 A | * | 11/2000 | Schalk | 604/247 |
| 6,953,450 B2 | * | 10/2005 | Baldwin et al. | 604/248 |

* cited by examiner

*Primary Examiner*—Melissa A. McCorkle
(74) *Attorney, Agent, or Firm*—Frank L. Kubler

(57) ABSTRACT

A flow rate selection valve includes a gate cylinder having a gate cylinder rotational axis and having at least two flow rate determining passageways and passing laterally through the gate cylinder at orientations angularly displaced from each other and having cylinder rotation structure; and a valve housing containing a flow passageway and having a cylinder receiving bore intersecting the flow passageway into which the gate cylinder is rotatably and sealingly mounted, the gate cylinder dividing the flow passageway into a passageway inlet end and a passageway outlet end, the flow passageway containing a passageway registration barrier extending across the flow passageway and sealingly abutting the gate cylinder and having several flow ports with different minimum diameters, each flow port positioned to register with one of the flow rate determining passageway.

10 Claims, 3 Drawing Sheets

MULTIPLE FLOW RATE SELECTION VALVE

BACKGROUND OF THE INVENTION

1. Field of the Invention

The present invention relates generally to the field of medication administration devices. More specifically the present invention relates to a flow rate selection valve such as for placement between a piercing tube structure referred to as a spike structure for piercing and draining solution from a standard intravenous bag and a drip chamber which opens into an intravenous line. The valve includes a gate cylinder having at least two flow rate determining passageways and passing diametrically through the gate cylinder at orientations angularly displaced from each other, and having a rotation engagement structure preferably in the form of a finger grip structure at one cylinder end for gate cylinder rotation; and which further includes a valve housing having a flow passageway and having a cylinder receiving bore intersecting and preferably perpendicular to the flow passageway into which the gate cylinder is rotatably and sealingly mounted, dividing the flow passageway into a passageway inlet end and a passageway outlet end. A passageway registration barrier extends across the passageway outlet end and sealingly fits partly around and against the gate cylinder and has several flow ports, each flow port corresponding to and registering with one of the flow rate determining passageways such that only one flow port registers with one rate determining passageway at a time.

The flow ports have different minimum diameters so that selection of the rate determining passageway and its corresponding flow port selects one of several available flow rates through the valve. Alternatively, the flow rate determining passageways have different minimum diameters, once again so that selection of a given flow rate determining passageway selects one of several available flow rates through the valve.

The standard spike structure is understood to include a tubular inlet passageway having a bag piercing tube upper end, a tubular spike structure body and a spike structure outlet port surrounded by a downwardly opening spike structure perimeter slot. The standard drip chamber is understood to include a tubular chamber side wall with a side wall upper end terminating in a side wall upper rim defining a drip chamber inlet opening, and a side wall lower end terminating in a chamber bottom wall with a drip chamber outlet opening encircled by a downwardly extending intravenous line fitting nozzle.

2. Description of the Prior Art

There are numerous tubular liquid delivering lines used in medical treatment, one of which is the intravenous line for delivering a solution from an intravenous bag to a catheter inserted into a vein of a patient. An intravenous bag piercing tube structure or spike structure pierces the intravenous bag and opens downwardly into a transparent drip chamber which in turn opens into the intravenous line. A problem with these prior intravenous assemblies has been that no suitable provision has been made for precisely selecting one of several desired flow rates from for a solution passing from the intravenous bag into the line.

It is thus an object of the present invention to provide a flow rate selection valve for liquid deliver lines such as intravenous lines which provides several different, precise and individually selectable flow rates.

It is another object of the present invention to provide such a flow rate selection valve having an inlet end which sealingly fits to a standard spike structure and an outlet end which sealingly fits to a standard drip chamber to regulate flow from the spike structure to the drip chamber.

It is still another object of the present invention to provide such a flow rate selection valve which is suitable for a wide variety of liquid delivery applications.

It is finally an object of the present invention to provide such a flow rate selection valve which is safe, reliable, inexpensive to manufacture and easy to connect and use.

SUMMARY OF THE INVENTION

The present invention accomplishes the above-stated objectives, as well as others, as may be determined by a fair reading and interpretation of the entire specification.

A flow rate selection valve, including a gate cylinder having a gate cylinder rotational axis and having at least two flow rate determining passageways and passing laterally through the gate cylinder at orientations angularly displaced from each other and having gate cylinder rotation structure for receipt of torque about the gate cylinder rotational axis; and a valve housing containing a flow passageway and having a cylinder receiving bore intersecting the flow passageway into which the gate cylinder is rotatably and sealingly mounted, the gate cylinder dividing the flow passageway into a passageway inlet end and a passageway outlet end, the flow passageway containing a passageway registration barrier extending across the flow passageway and sealingly abutting the gate cylinder and having several flow ports with different minimum diameters, each flow port being positioned to correspond to and register with one of the flow rate determining passageways; so that rotating the gate cylinder with the gate cylinder rotation structure causes the flow passageways to register sequentially and individually with a corresponding the flow port.

The gate cylinder has a gate cylinder end and the gate cylinder rotation structure preferably includes a finger grip structure connected to the gate cylinder end. The finger grip structure preferably includes a knob. The flow rate selection valve preferably additionally including flow rate indicia on the valve housing adjacent to the knob for indicating which flow rate determining passageway is oriented to pass fluid from the passageway inlet end to the passageway outlet end. The cylinder receiving bore is substantially perpendicular to the flow passageway. The passageway inlet end preferably is tubular and sized to sealing fit and engage a standard spike structure, and the passageway outlet end preferably is tubular and has a downwardly opening perimeter slot sized to snugly and sealingly receive an upper rim of a standard drip chamber.

The flow rate determining passageways preferably pass through the gate cylinder substantially diametrically. The gate cylinder preferably includes three flow rate determining passageways.

An intravenous assembly includes a spike structure including a tubular inlet passageway having a bag piercing upper end and a spike structure outlet opening; a drip chamber having a drip chamber inlet opening and a drip chamber outlet opening and a tubular chamber side wall; a flow rate selection valve including a gate cylinder having a gate cylinder rotational axis and having at least two flow rate determining passageways and passing laterally through the gate cylinder at orientations angularly displaced from each other a certain number of degrees and having gate cylinder rotation structure for receipt of torque about the gate cylinder rotational axis, and a valve housing containing a flow passageway and having a cylinder receiving bore intersecting the flow passageway into which the gate cylinder is rotatably and sealingly mounted, the gate cylinder dividing the flow passageway into a passageway inlet end and a passageway outlet end, the flow passageway containing a passageway registration barrier extending across the flow passageway and sealingly abutting the gate cylinder and having a plurality of flow ports with different minimum diameters, each flow port being positioned to correspond to and register with one of the flow rate determining passageways, such that rotating the gate cylinder with the gate cylinder rotation structure causes the flow passageways to register sequentially and individually with a corresponding the flow port.

A flow rate selection valve is further provided, including a gate cylinder having a gate cylinder rotational axis and having at least two flow rate determining passageways with different minimum diameters and passing laterally through the gate cylinder at orientations angularly displaced from each other and having a gate cylinder rotation structure for receipt of torque about the gate cylinder rotational axis; and a valve housing containing a flow passageway and having a cylinder receiving bore intersecting the flow passageway into which the gate cylinder is rotatably and sealingly mounted, the gate cylinder dividing the flow passageway into a passageway inlet end and a passageway outlet end, the flow passageway containing a passageway registration barrier extending across the flow passageway and sealingly abutting the gate cylinder and having several flow ports, each flow port being positioned to correspond to and register with one of the flow rate determining passageways; so that rotating the gate cylinder with the gate cylinder rotation structure causes the flow passageways to register sequentially and individually with a corresponding the flow port.

BRIEF DESCRIPTION OF THE DRAWINGS

Various other objects, advantages, and features of the invention will become apparent to those skilled in the art from the following discussion taken in conjunction with the following drawings, in which:

FIG. 3 is a cross-sectional side view of the preferred flow rate selection valve and of a standard spike structure positioned for fitting onto the flow rate selection valve, showing the perimeter channel for receiving the upper rim of a drip chamber, but for the present invention receiving instead the . . .

DETAILED DESCRIPTION OF THE PREFERRED EMBODIMENTS

Figure 1:
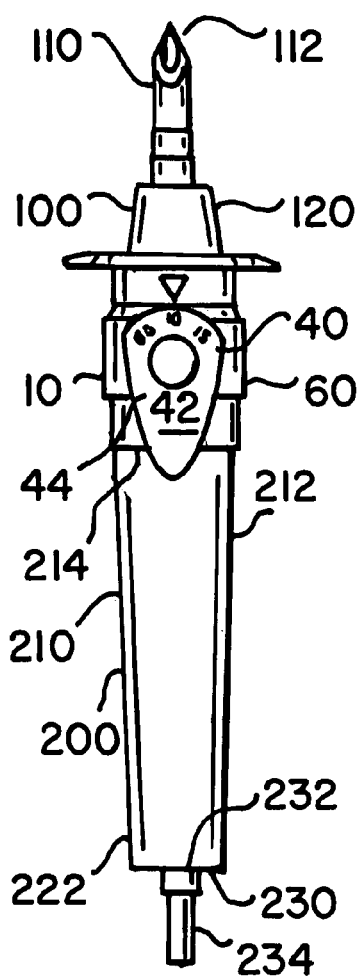
FIG. 1 is a side view of the preferred flow rate selection valve mounted between and controlling fluid communication between a spike structure for piercing and draining solution from a standard intravenous bag and a drip chamber which opens into an intravenous line.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings, wherein like characteristics and features of the present invention shown in the various FIGURES are designated by the same reference numerals.

First Preferred Embodiment

Figure 2:
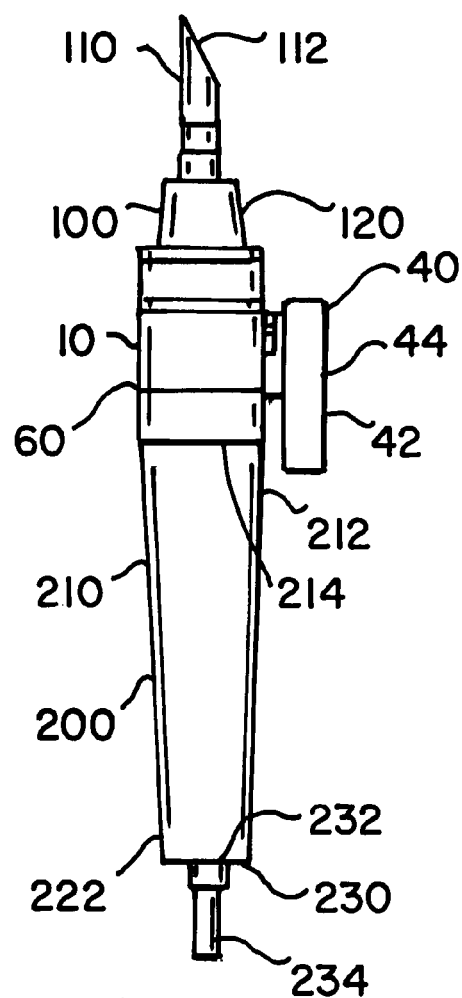
FIG. 2 is a laterally projected side view of the assembly of FIG. 1.
Figure 3:
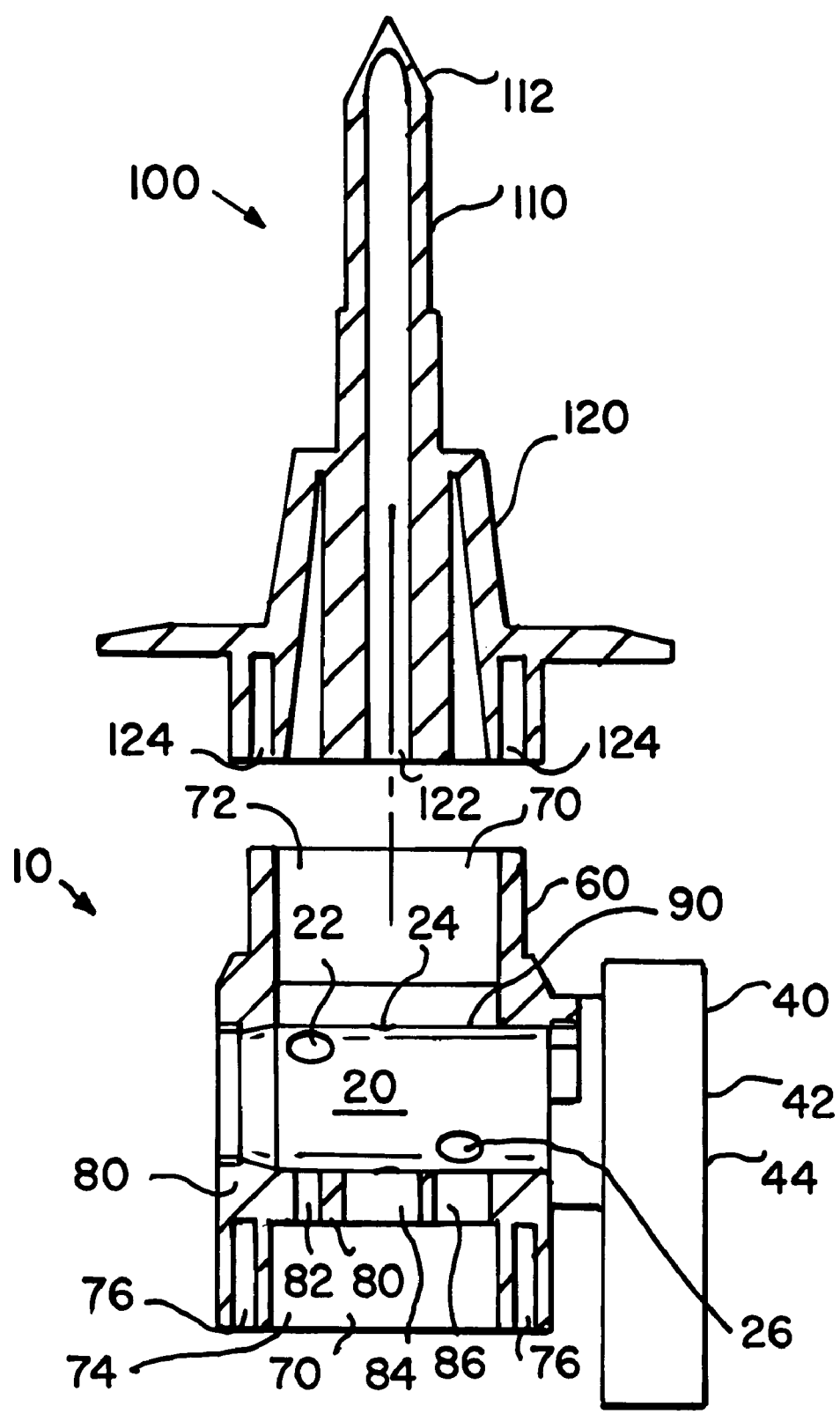
Figure 5:
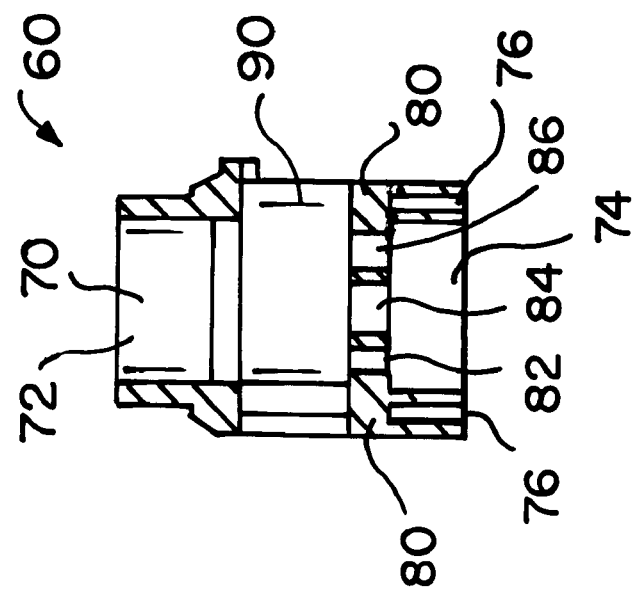
FIG. 5 is a cross-sectional side view of the flow rate selection valve of FIG. 1.
Figure 4:
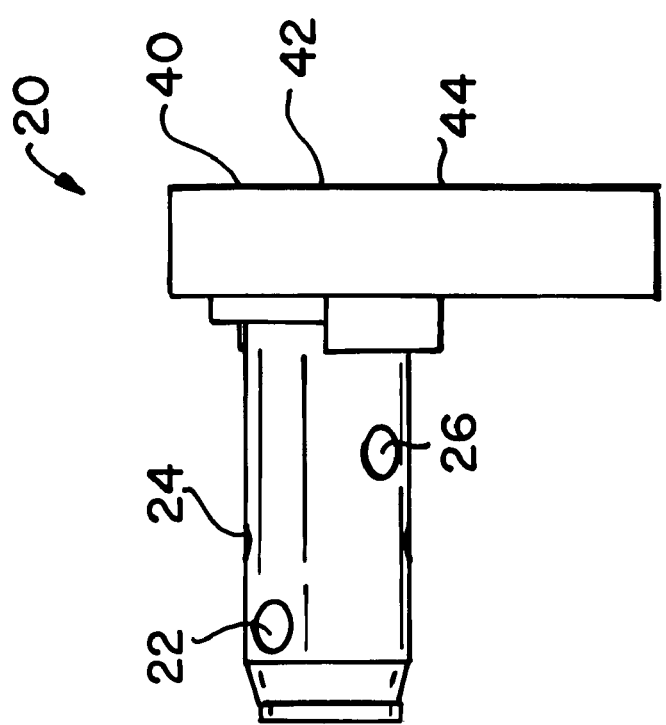
FIG. 4 is a side view of the gate cylinder and finger grip structure, shown separately from the valve housing.

Referring to FIGS. 1–5, a flow rate selection valve 10 is disclosed for placement between a solution containing standard intravenous bag piercing tube structure referred to herein as a spike structure 100 and a drip chamber 200 which opens into an intravenous line L. The valve 10 includes a gate cylinder 20 having at least two and preferably three flow rate determining passageways 22, 24 and 26 and passing laterally through the gate cylinder 20 at orientations angularly displaced from each other and having a rotation engagement structure 40, preferably in the form of a finger grip structure at one cylinder end; and including a valve housing 60 having a flow passageway 70 and having a cylinder receiving bore 90 intersecting and preferably perpendicular to the flow passageway into which the gate cylinder 20 is rotatably and sealingly mounted dividing the flow passageway into a passageway inlet end 72 and a passageway outlet end 74. The rotation engagement structure 40 is accessible for engagement and receipt of torque about the longitudinal cylinder rotational axis RA of the gate cylinder 20. A passageway registration barrier 80 extends across the passageway outlet end and sealingly fits partly around and abuts the gate cylinder 20 and has several flow ports 82, 84 and 86, each flow port corresponding to and registering with one of the flow rate determining passageways 22, 24 or 26 such that only one flow port registers with one rate determining passageway at a time. The flow ports 82, 84 and 86 have different minimum diameters so that selection of the rate determining passageway 22, 24 or 26 and its corresponding flow port 82, 84 or 86 selects one of several available flow rates through valve 10. Alternatively, the flow rate determining passageways 22, 24 and 26 have different minimum diameters, once again so that selection of a given flow rate determining passageway 22, 24 or 26 selects one of several available flow rates through valve 10.

The finger grip structure 40 preferably includes an elongate flow selection knob 42 having a longitudinal axis perpendicular to the cylinder rotational axis RA. The flow selection knob 42 preferably has a knob outward face 44 marked with flow rate selection indicia I corresponding in rotational position with the flow rate determining passageways 22, 24 and 26 and the housing 60 has a selection marker 62 adjacent to the flow selection knob 42. As a result, rotating flow selection knob 42 causes flow rate selection indicia I to each individually and sequentially register with the selection marker M when the corresponding flow rate determining passageway 22, 24 or 26 is oriented to place the passageway inlet end 72 into fluid communication with the passageway outlet end 74 and that thereby regulate the flow rate through the valve 10.

The standard spike structure 100 is understood to include a tubular inlet passageway 110 having a bag piercing upper end 112, a tubular spike structure body 120 and a spike structure outlet port 122 surrounded by a downwardly opening spike structure perimeter slot 124. The standard drip chamber 200 is understood to include a tubular chamber side wall 210 with a side wall upper end 212 terminating in an upper rim 214 defining a drip chamber inlet opening, and a side wall lower end 222 terminating in a chamber bottom wall 230 with a drip chamber outlet opening 232 encircled by a downwardly extending intravenous line engaging nozzle 234.

The valve passageway inlet end 72 is tubular and is sized to snugly and sealing fit into and thereby engage the perimeter slot 124 in the spike structure 100, and the passageway outlet end 74 is also tubular and has a perimeter slot 76 sized to snugly and sealingly receive and thereby engage the perimeter side wall upper rim 214 of a standard drip chamber 200. The gate cylinder 20 preferably includes the three flow rate determining passageways 22, 24 and 26, although providing other numbers of such passageways is contemplated.

While the invention has been described, disclosed, illustrated and shown in various terms or certain embodiments or modifications which it has assumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim:

1. A flow rate selection valve, comprising:
a gate cylinder having a gate cylinder rotational axis and having at least two flow rate determining passageways and passing laterally through said gate cylinder at orientations angularly displaced from each other and having gate cylinder rotation means for receipt of torque about said gate cylinder rotational axis;
and a valve housing containing a flow passageway and having a cylinder receiving bore intersecting said flow passageway into which said gate cylinder is rotatably and sealingly mounted, said gate cylinder dividing said flow passageway into a flow passageway inlet end and a flow passageway outlet end, said flow passageway containing a passageway registration barrier extending across said flow passageway and sealingly abutting said gate cylinder and having a plurality of flow ports with different minimum diameters, each said flow port being positioned to correspond to and register with one of said flow rate determining passageways and said flow ports being in simultaneous fluid communication with one of: said flow passageway inlet end and said flow passageway outlet end;
such that rotating said gate cylinder with said gate cylinder rotation means causes said flow rate determining passageways to register sequentially and individually with corresponding said flow ports, and thereby places said flow passageway outlet end sequentially in fluid communication with said flow passageway inlet end.

2. The flow rate selection valve of claim 1, wherein said gate cylinder has a gate cylinder end and wherein said gate cylinder rotation means comprises a finger grip structure connected to said gate cylinder end.

3. The flow rate selection valve of claim 2, wherein said finger grip structure comprises a knob.

4. The flow rate selection valve of claim 3, additionally comprising flow rate indicia on said valve housing adjacent to said knob for indicating which flow rate determining passageway is oriented to pass fluid from said passageway inlet end to said passageway outlet end.

5. The flow rate selection valve of claim 1, wherein said cylinder receiving bore is substantially perpendicular to said flow passageway.

6. The flow rate selection valve of claim 1, wherein said passageway inlet end is tubular and sized to sealingly fit and engage a standard spike structure, and wherein said passageway outlet end is tubular and has a downwardly opening perimeter slot sized to snugly and sealingly receive an upper rim of a standard drip chamber.

7. The flow rate selection valve of claim 1, wherein said flow rate determining passageways pass through said gate cylinder substantially diametrically.

8. The flow rate selection valve of claim 1, wherein said gate cylinder comprises three flow rate determining passageways.

9. An intravenous assembly comprising:
a spike structure comprising a tubular inlet passageway having a bag piercing upper end and a spike structure outlet opening;
a drip chamber having a drip chamber inlet opening and a drip chamber outlet opening and a tubular chamber side wall;
a flow rate selection valve comprising a gate cylinder having a gate cylinder rotational axis and having at least two flow rate determining passageways and passing laterally through said gate cylinder at orientations angularly displaced from each other and having gate cylinder rotation means for receipt of torque about said gate cylinder rotational axis, and a valve housing containing a flow passageway and having a cylinder receiving bore intersecting said flow passageway into which said gate cylinder is rotatably and sealingly mounted, said gate cylinder dividing said flow passageway into a flow passageway inlet end and a flow passageway outlet end, said flow passageway containing a passageway registration barrier extending across said flow passageway and sealingly abutting said gate cylinder and having a plurality of flow ports with different minimum diameters, each said flow port being positioned to correspond to and register with one of said flow rate determining passageways and said flow ports being in simultaneous fluid communication with one of: said flow passageway inlet end and said flow passageway outlet end, such that rotating said gate cylinder with said gate cylinder rotation means causes said flow rate determining passageways to register sequentially and individually with corresponding said flow ports, and thereby places said flow passageway outlet end sequentially in fluid communication with said flow passageway inlet end.

10. A flow rate selection valve, comprising:
a gate cylinder having a gate cylinder rotational axis and having at least two flow rate determining passageways with different minimum diameters and passing laterally through said gate cylinder at orientations angularly displaced from each other and having gate cylinder rotation means for receipt of torque about said gate cylinder rotational axis;
and a valve housing containing a flow passageway and having a cylinder receiving bore intersecting said flow passageway into which said gate cylinder is rotatably and sealingly mounted, said gate cylinder dividing said flow passageway into a flow passageway inlet end and a flow passageway outlet end, said flow passageway containing a passageway registration barrier extending across said flow passageway and sealingly abutting said gate cylinder and having a plurality of flow ports, each said flow port being positioned to correspond to and register with one of said flow rate determining passageways and said flow ports being in simultaneous fluid communication with one of: said flow passageway inlet end and said flow passageway outlet end;
such that rotating said gate cylinder with said gate cylinder rotation means causes said flow rate determining passageways to register sequentially and individually with corresponding said flow ports, and thereby places said flow passageway outlet end sequentially in fluid communication with said flow passageway inlet end.

* * * * *